United States Patent
Furutani et al.

[11] Patent Number: 5,998,340
[45] Date of Patent: Dec. 7, 1999

[54] LUBRICANT AND MAGNETIC RECORDING MEDIUM USING THE SAME

[75] Inventors: Takahiro Furutani, Otokuni-gun; Sayaka Shinomoto, Kyoto; Kazushi Miyata, Mishima-gun, all of Japan

[73] Assignee: Hitachi Maxell, Ltd., Osaka-fu, Japan

[21] Appl. No.: 09/035,947

[22] Filed: Mar. 6, 1998

[30] Foreign Application Priority Data

Mar. 7, 1997 [JP] Japan ................................. 9-070746

[51] Int. Cl.$^6$ ............... C10M 105/38; C10M 105/36; C07C 69/34
[52] U.S. Cl. ............... 508/495; 508/485; 508/496; 428/65.4; 428/65.8; 560/192; 560/223
[58] Field of Search ................... 508/485, 495, 508/496; 428/65.4, 65.8; 560/192, 223

[56] References Cited

U.S. PATENT DOCUMENTS

| | | | |
|---|---|---|---|
| 3,223,636 | 12/1965 | Metro et al. | 508/496 |
| 3,282,840 | 11/1966 | Foster, Jr. et al. | 508/495 |
| 3,330,762 | 7/1967 | Wendler et al. | 252/32.5 |
| 3,360,547 | 12/1967 | Wilson et al. | 260/485 |
| 4,786,427 | 11/1988 | Dare-Edwards | 508/496 |
| 5,227,516 | 7/1993 | Tohzuka et al. | 560/182 |
| 5,286,397 | 2/1994 | Schmid et al. | 508/496 |
| 5,700,541 | 12/1997 | Okita et al. | 428/65.4 |

FOREIGN PATENT DOCUMENTS

| | | |
|---|---|---|
| 60-085427 | 5/1985 | Japan . |
| 2210615 | 8/1990 | Japan . |
| 4368621 | 12/1992 | Japan . |
| 6004855 | 1/1994 | Japan . |
| 6274858 | 9/1994 | Japan . |

*Primary Examiner*—Jerry D. Johnson
*Attorney, Agent, or Firm*—Birch, Stewart, Kolasch & Birch, LLP

[57] ABSTRACT

A lubricant containing a branched aliphatic diester of the general formula: $R_1R_2R_3C-(CH_2)_n-X-R-X'-(CH_2)_n-CR_4R_5R_6$ in which $R_1$ to $R_6$ independently represent a hydrocarbon group having 1–18 carbon atoms; R is a fluorinated hydrocarbon group having 6 to 18 carbon atoms; either one of X and X' represent either one of —OCO— and —COO—, while the other of X and X' represent the other of —OCO— and —COO—; and n is an integer from 0 to 6, and optionally an aliphatic amine of the general formula: $R_7NR_8R_9$ in which $R_7$, $R_8$ and $R_9$ independently represent a hydrogen atom or a hydrocarbon group having 1 to 26 carbon atoms.

12 Claims, 1 Drawing Sheet

LUBRICANT AND MAGNETIC RECORDING MEDIUM USING THE SAME

BACKGROUND OF THE INVENTION

1. Field of the Invention

The present invention relates to a lubricant and a magnetic recording medium using the same. More specifically, the lubricant allows for low friction, low abrasion sliding between two touching solids, regardless of high or low speeds, or high or low loads, and under all environmental conditions such as high or low temperatures, or high or low humidity. The present invention also pertains to the use of this lubricant in magnetic recording media having excellent durability and traveling performance.

2. Prior Art

With the aim of allowing for low friction, low abrasion sliding between two touching solids and lengthening the usage period of instruments and equipment, development is being carried out on the hardening of solid surfaces and on lubricants. The demand for size reduction in the OA instrument field is particularly strong, and every year precise mechanisms in the slidable portion area are introduced. In the future, precision parts will require increasing reductions in friction and abrasion when the sliding begins, ends and is in progress, and a greater reduction in the load on the motor, etc., than is provided by the current slidable instruments, when they operate continuously or discontinuously under a broad range of environmental conditions. In conventional protective lubrication systems, the slidable position has a hard surface layer which is difficult to abrade, and grease, oil, half-solid or liquid lubricants are used.

However, in precision equipment in which smoothing of the touching portions have been completed, a lubricant which allows low friction, low abrasion sliding between two touching solids regardless of high or low speeds, and high or low loads cannot be obtained. Thus, the problems of poor starting, or a sudden accidental increase in the friction force when sliding cannot be avoided.

When compared to coating type magnetic recording media, ferromagnetic metal thin film type magnetic recording media, which are made by depositing ferromagnetic metals or their alloys, etc. on a non-magnetic support by vacuum deposition, etc., can easily increase the anti-magnetization properties and decrease the thickness of the media, and have good high-density recording properties. On the other hand, they have disadvantages in that the coefficient of friction at the magnetic head increases, and they are easily abraded or damaged, since they use no tough binder resin, and the ferromagnetic metal thin film layer or the protective membrane has good surface smoothness. Thus, their durability and traveling performance are inferior.

Accordingly, durability and traveling performance are improved by the provision of various lubricants, such as ester-type lubricants, on the ferromagnetic metal thin film (see U.S. Pat. Nos. 4,735,848, 5,356,726 and 5,376,465, and Japanese Kokai Patent Publication Nos. 60-85427, 2-210615, 4-368621 and 6-274858).

However, the problem of smudging on the magnetic head or "drop out" has not been solved. The durability and traveling performance are insufficient, especially under high temperature and humidity conditions.

SUMMARY OF THE INVENTION

One object of the present invention is to provide a lubricant that can allow the low friction, low abrasion sliding between two touching solids regardless of high or low speeds, or high or low loads, even in the smoothing of the portion at the touching position, thereby ensuring future precision.

Another object of the present invention is to provide a magnetic recording medium which has excellent durability and traveling performance.

According to the first aspect, the present invention provides a lubricant comprising a branched aliphatic diester of the general formula:

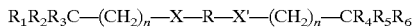

wherein $R_1$ to $R_6$ are the same or different and represent a hydrocarbon group having 1–18 carbon atoms;
R is a hydrocarbon group or a fluorinated hydrocarbon group having 6 to 18 carbon atoms;
either one of X and X' represent either one of —OCO— and —COO—, while the other of X and X' represent the other of —OCO— and —COO—; and
n is an integer from 0 to 6.

The fluorinated hydrocarbon groups include perfluorinated hydrocarbon groups and partially fluorinated hydrocarbon groups.

According to the second aspect, the present invention provides a lubricant comprising a branched aliphatic diester of the general formula:

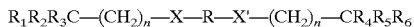

wherein $R_1$ to $R_6$, R, X, X' and n are the same as defined above,
and an aliphatic amine of the general formula:

wherein $R_7$, $R_8$ and $R_9$ are the same or different and represent a hydrogen atom or a hydrocarbon group having 1 to 26 carbon atoms.

According to the third aspect, the present invention provides a magnetic recording medium comprising a non-magnetic support and a magnetic layer on at least one side of said non-magnetic support, wherein the magnetic medium contains a lubricant which comprises a branched aliphatic diester of the general formula:

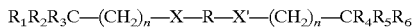

wherein $R_1$ to $R_6$, R, X, X' and n are the same as defined above
within or on the surface of the magnetic layer.

According to the fourth aspect, the present invention provides a magnetic recording medium comprising a non-magnetic support and a magnetic layer on at least one side of said non-magnetic support wherein the medium contains a lubricant which comprises a branched aliphatic diester of the general formula:

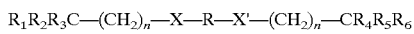

wherein $R_1$ to $R_6$, R, X, X' and n are the same as defined above,
and an aliphatic amine of the general formula:

wherein $R_7$, $R_8$ and $R_9$ are the same as defined above within or on the surface of the magnetic layer.

DETAILED DESCRIPTION OF THE INVENTION

Figure 1:
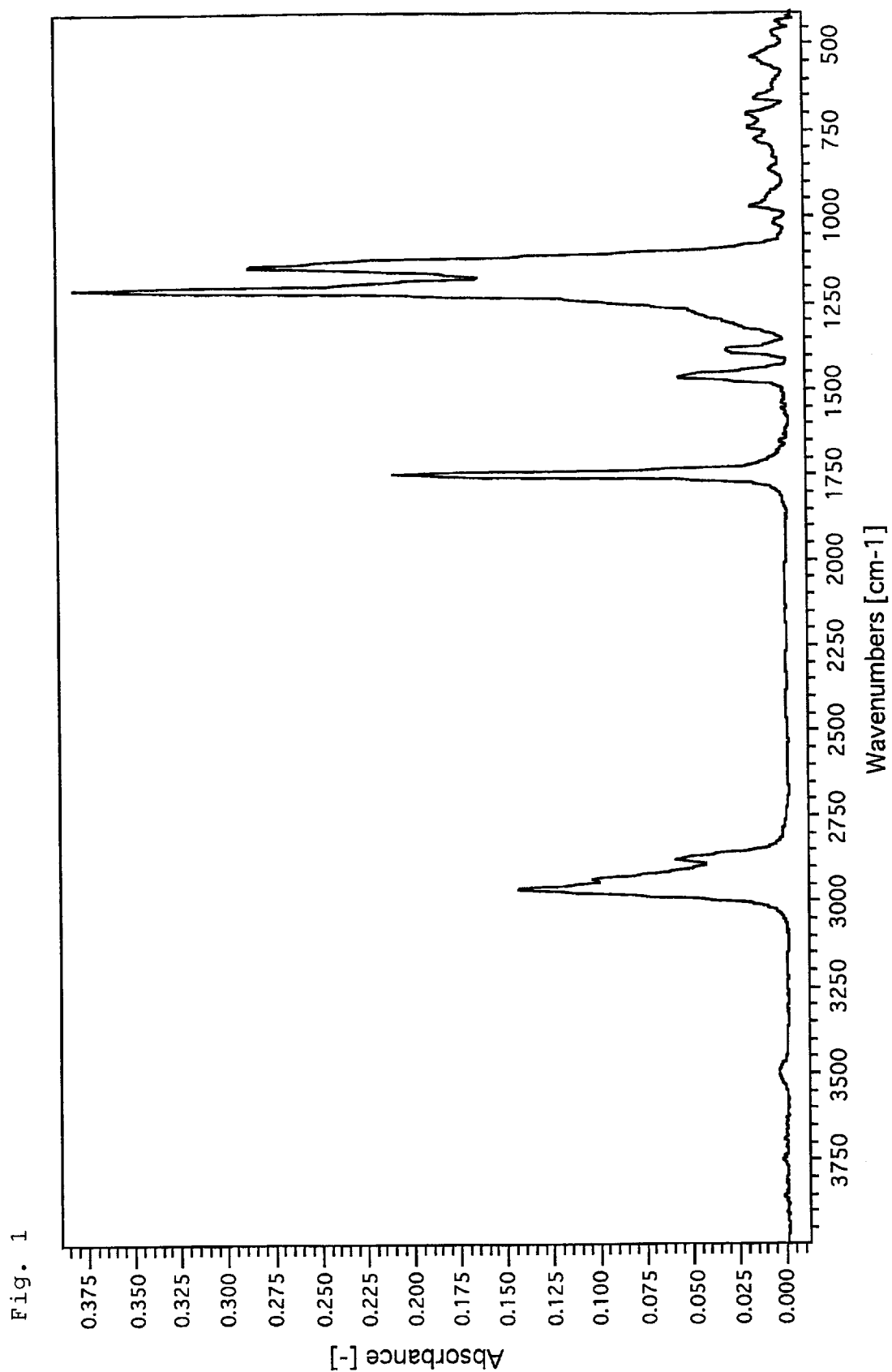
FIG. 1 is an IR spectrum of the branched aliphatic diester prepared in Preparation Example 1.

In the present invention, the branched aliphatic diester, which has two ester groups per molecule and is represented by the general formula:

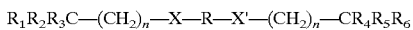

$$R_1R_2R_3C-(CH_2)_n-X-R-X'-(CH_2)_n-CR_4R_5R_6$$

wherein $R_1$ to $R_6$, R, X, X' and n are the same as defined above, has excellent lubrication properties and, when used as a lubricant, can allow two touching solid surfaces to slide with low friction and low abrasion.

The branched aliphatic diester has good resistance to hydrolysis, since it has the branched groups. Several experiments have been carried out with varying temperature, moisture and oxygen concentration in an atmosphere, for revealing the mechanism of decomposition of the ester-type lubricants, and it has been found that the presence of water accelerates the decomposition, and thus the cause for the decomposition is a hydrolysis reaction. A hydrolysis reaction occurs as $OH^-$ ions or $H_3O^+$ ions attack the carbonyl group of the ester. Because the branched aliphatic diester used in the present invention has a very bulky branched hydrocarbon group close to the carbonyl group, there is a large steric hindrance and, as a result, hydrolysis of the ester linkage is not easily initiated even under high temperature and humidity conditions, and the diester is chemically stable. When using it in magnetic recording media, the formation of lubricant-modification products causing dirt marks on the head or "drop out" can be reduced.

Moreover, the branched aliphatic diester can be stable and firmly adsorbed on the surface of the ferromagnetic metal thin film or protective membrane due to the presence of two ester groups per molecule. As a result, the lubricant can remain stable and can demonstrate favorable sliding characteristics without being removed from the sliding surface even under high load conditions such as at the commencement of sliding.

Therefore, the branched aliphatic diester can allow sliding between two touching solids with low friction and low abrasion regardless of high or low speeds, or high or low loads. It is strongly adsorbed and remains stable on the magnetic layer surface or on the surface of the protective membrane, or it is included in a stable state inside the magnetic layer, when used for magnetic recording media. Accordingly, the excellent lubricating function is sufficiently demonstrated along with a significant reduction in dirty marks on the magnetic head or "drop out", and the durability and traveling performance of the magnetic recording media can also be sufficiently improved.

The branched aliphatic diester can sufficiently control hydrolysis, even under high temperature and humidity conditions, due to steric hindrance, because it has a tertiary carbon atom in a position adjacent or close to the carbonyl group. There may be a hydrocarbon group between the tertiary carbon and the carbonyl group. However, if this hydrocarbon group has 7 or more carbon atoms, then the efficacy of the steric hindrance caused by the branched hydrocarbon group cannot be sufficiently obtained because the tertiary carbon and the carbonyl group are too far away from each other. Therefore, there are preferably 0–6 carbon atoms in the hydrocarbon group between the tertiary carbon and the carbonyl group, more desirably, three or fewer and, at best, none.

Each of the individual hydrocarbon groups $R_1$, $R_2$, $R_3$, $R_4$, $R_5$, and $R_6$, which are bonded to the tertiary carbons of the branched aliphatic diester, preferably have no fewer than 1 but no more than 18 carbon atoms. This is irrespective of whether they are saturated or unsaturated, straight or branched or cyclic. Among them, the straight hydrocarbon is preferable. Having the hydrocarbon group within the molecule allows for easy treatment as it can be dissolved in a general-purpose solvent, which may help with cost reductions.

The R of the branched aliphatic diester is preferably a fluorinated carbon group or a hydrocarbon group with 6 to 18 carbon atoms. To reduce the surface free energy and to obtain favorable lubrication characteristics, a fluorinated hydrocarbon group is desirable. Furthermore, to obtain lubrication characteristics, it preferably has 6 or more carbon atoms, but no more than 18 carbon atoms. Nineteen or more carbon atoms cause an undesirable increase in the viscosity of the lubricant. The hydrocarbon or fluorinated hydrocarbon group may be a straight or branched group, and a straight hydrocarbon or fluorinated hydrocarbon group is preferable.

The branched aliphatic diester used in the present invention preferably has at least 20 carbon atoms in total. When the total number of constituent carbon atoms is 19 or less, a reduction in the lubrication occurs due to evaporation, and the sliding characteristics at high temperatures and after maintaining high temperatures are insufficient. More desirable are no fewer than 24 but no more than 130 carbon atoms.

The branched aliphatic diester may be synthesized by any process. As an example of an industrially viable synthesis, it can simply be synthesized by the reaction of, for example, a diol with a chloride of a tertiary fatty acid, or a dicarboxylic acid with a tertiary alcohol.

For this, as a diol, the following compounds can be used: 1H,1H,2H,3H, 3H-perfluorononane-1,2-diol, 1H,1H,2H, 3H,3H-perfluoroundecane-1,2-diol, 1H,1H,6H,6H-perfluoro-1,6-hexanediol, 1H,1H,8H,8H-perfluoro-1,8-octanediol, 1H,1H,10H,10H-perfluoro-1,10-decanediol, 1H,1H,12H,12H-perfluoro-1,12-dodecanediol, 2,2-bis(4-hydroxyphenyl)-hexafluoropropane (F-TECH Co., Ltd. or HYDRUS Chemicals Ltd.), FOMBLIN Z DOL (AUSIMONT), 1,8-octanediol, 1,10-decanediol or 1,12-dodecanediol, and the like.

As the tertiary fatty acid, the following products may be used industrially:

Versatic 5, Versatic 10, Versatic 911, and Versatic 1516 (all available from Shell Company Ltd.); Ekacid 9 and Ekacid 13 (all available from Idemitsu Petrochemical Co., Ltd.); neodecanoic acid (available from Exxon); and the like. These tertiary fatty acids (except neodecanoic acid) are mixtures of the following tertiary fatty acids: 2-isopropyl-2,3-dimethylheptanoic acid; 2-ethyl-2,3,3-trimethylbutanoic acid; 2,2,4,4,-tetramethylpentanoic acid; 2,2,3,4-tetramethylpentanoic acid; 2,2,3,3-tetramethylpentanoic acid; 2-isopropyl-2,3,5,5-tetramethylhexanoic acid; 2,3,4-trimethyl-2-neopentylpentanoic acid; 2,2,4,4,6,6-hexamethylheptanoic acid; 2,4,4-trimethyl-2-tert-pentylpentanoic acid; 2-ethyl-2,3,3,5,5-pentamethylhexanoic acid; and so on.

Perfluorosebacic acid and perfluoro-1,10-decane dicarboxylic acid (available from HYDRUS Chemical Co., Ltd.), 1,8-octanedicarboxylic acid, 1,10-decanedicarboxylic acid, 1,12-dodecanedicarboxylic acid, and the like can be used as the dicarboxylic acid. 2-Methyl-2-pentanol and 2-methyl-2-hexanol and the like can be used as the tertiary aliphatic alcohol.

Furthermore, when an aliphatic amine of the general formula $R_7N(R_8)R_9$ wherein $R_7$, $R_8$ and $R_9$ are the same as defined is added to the branched aliphatic diester, then there may be an improvement in the sliding properties under high temperature and pressure.

Examples of the aliphatic amine are laurylamine, stearylamine, oleylamine, dilaurylamine, distearylamine, dioleylamine, phenyldodecylamine, N-methylstearylamine, N,N-dimethylstearylamine, tridodecylamine, tridecylamine, trioctylamine, or the like. Among them, stearylamine, oleylamine, and N,N-dimethylamine are more desirable.

The aliphatic amine is preferably added in a molar ratio of the aliphatic amine to the branched aliphatic diester of between 100:1 and 0.01:1, and more preferably in a ratio of between 10:1 and 0.1:1 respectively.

The branched aliphatic diester, or a lubricant comprising a branched aliphatic diester and an aliphatic amine may be used together with other lubricants where necessary. For example, they may be suitably used together with generally used lubricants such as fatty acids or their metal salts, aliphatic diesters, aliphatic amides, aliphatic alcohols, monosulfides, paraffins, silicone compounds, esters of aliphatic compounds and fluorides, perfluoropolyether, polytetrafluoroethylene, and the like. In this case, the general lubricant is preferably added to the branched aliphatic diester or to the lubricant comprising a branched aliphatic diester and an aliphatic amine, in a molar ratio of between 100:1 and 0.01:1, and more desirably in a molar ratio of between 10:1 and 0.1:1 respectively.

Furthermore, the lubricants may also be used together with phosphorus extreme pressure agents such as trioleyl phosphate, sulfur extreme pressure agents such as benzyl disulfide, halogen extreme pressure agents such as allyl bromide, and organometallic extreme pressure agents such as zinc di-isobutyl dithiophosphate, and the like.

When the lubricant is provided on the magnetic recording layer or the protective membrane, it is dissolved in a general-purpose solvent such as an alcohol, a hydrocarbon, a ketone, an ether, or the like, and this solution is applied or sprayed onto the pre-formed magnetic layer or the protective membrane, and then dried. Alternatively, the magnetic layer or the protective membrane is immersed in the above-mentioned solution and then dried.

For this, the following can be given as specific examples of a general-purpose organic solvent: n-hexane, heptane, octane, decane, dodecane, benzene, toluene, xylene, cyclohexane, methyl ethyl ketone, methyl isobutyl ketone, methanol, ethanol, isopropanol, diethyl ether, tetrahydrofuran, and cyclohexanone.

When the magnetic layer is a ferromagnetic metal thin film layer, a protective membrane may be formed on top of the ferromagnetic metal thin film layer by vacuum deposition, sputtering, or plasma coating, etc. This protective membrane may be an inorganic membrane comprising carbon, silicon dioxide, zirconium oxide, chromium oxide or an organic membrane. Moreover, the ferromagnetic metal thin film layer may also have a very small amount of water adhered on its surface and/or may be coated with rust proofing agents such as benzotriazole, etc.

Furthermore, the surface of the protective membrane may undergo oxygen and ammonia plasma treatment. With plasma treatment, while the protective membrane surface is being purified, chemically active species within the plasma can accumulate and the lubricants can become more stable without reducing the hardness of the protective membrane.

The lubricants can be made more stable through the treatment with glow discharge, ultraviolet irradiation, and heat treatments, and so on. These treatments may be conducted before or after the adhesion of the lubricants. Furthermore, they may even be conducted after the rinsing off with solvents of any excess lubricant after the adhesion of the lubricants.

In the case of a coating type magnetic recording media, the lubricant may be applied by coating, spraying or immersion as described above. Alternatively, the lubricant can be added to the magnetic layer by blended the lubricant with a magnetic powder, binder resins, and organic solvents, along with other additives to make up the magnetic paint, applying this magnetic paint on top of a non-magnetic support by a suitable method, and then drying it.

An additional lubricant may be applied on top of the magnetic layer which has been thus constructed using the same methods mentioned above such as coating, spraying, immersion, and so on of the solutions containing the dissolved lubricant.

Any excess lubricant may be washed off with a solvent after adhesion. Furthermore, the lubricant may be applied on the opposite side of the magnetic layer, and transferred to the magnetic layer side.

The amount of the lubricants applied on top of the ferromagnetic metal thin film layer is preferably in the range of 0.5 to 20 mg/m$^2$ relative to the surface of the ferromagnetic metal thin film layer. When the lubricants are contained in the magnetic layer, the amount of the lubricant is within the range of 10–100 mg/m$^2$. With an amount of less than the lower limit, it is difficult to adhere the layer of lubricant evenly onto the surface of the ferromagnetic metal thin membrane layer and a sufficient improvement in the still durability cannot be obtained. Too much is also undesirable as it causes sticking between the magnetic head and the ferromagnetic metal thin film layer.

The amounts of lubricants applied and/or contained can be evaluated by immersing a magnetic tape, to which the lubricant has been applied in a solvent overnight, and then analyzing the extracted lubricant in the solvent by gas or liquid chromatography, or the like.

Plastics, such as polyethylene terephthalate, polyethylene naphthalate, polycarbonate, polyamide, polyimide, polyvinyl chloride, and the like, or aluminum or titanium alloys may be used as suitable non-magnetic supports. The non-magnetic support may be in any form, such as tapes, sheets, discs, cards, and so on, and it may even have lumps on the surface.

For the ferromagnetic metal thin film layer, the magnetic layer is formed from Co, Ni, Fe, Co—Ni, Co—Cr, Co—P, Co—Ni—P, Fe—Co—B, Fe—Co—Ni, Co—Ni—Fe—B, Fe—Ni, Fe—Co, Co—Pt, Co—Ni—Pt or various ferromagnetic materials made from the addition of oxygen to the above metal or alloys. These are adhered onto one or both sides of a non-magnetic support by a process such as vapor deposition, ion-plating, sputtering, plating, and the final thickness of the metal thin film layer is usually in the range of 0.03 $\mu$m and 1 $\mu$m.

For the coating type magnetic layer, it is formed according to the following process. A magnetic paint is prepared as a dispersion mixture of magnetic powder, binder resin, and organic solvent as well as other additives. This magnetic paint is applied onto a non-magnetic support by a suitable method such as spraying or roll coating or the like and then dried. The final thickness of the metal thin film layer is normally in the range of 0.05-10 $\mu$m.

As the magnetic powder for this, all magnetic powders known in the prior art may be used. Examples are oxide magnetic powders such as $\gamma$—$Fe_2O_3$, $Fe_3O_4$, an intermediate iron oxides of γ—$Fe_2O_3$ and $Fe_3O_4$, Co-containing γ—$Fe_2O_3$, Co-containing γ—$Fe_3O_4$, $CrO_2$, and barium ferrite, etc.; metal magnetic powders such as Fe, Co, and Fe—Ni—Cr alloys, etc.; and nitride type magnetic powders such as iron nitride, etc. For needle-like magnetic powders, those with an average particle size (major axis) normally in the range of 0.05–1 μm and an average axial ratio (average major axis length/average minor axis length) normally in the range of 5–10 are preferably used. For plate-like magnetic powders, those with an average major axis length normally in the range of 0.07–0.3 μm is preferably used.

As the binder resins, any binder resins used in magnetic recording media may be used. Examples are vinyl chloride-vinyl acetate copolymer, cellulose resin, polyurethane resin, polyester resin, polyvinyl butyral resin, polyacrylic resin, epoxy resin, phenol resin, polyisocyanate compounds, and the like.

All suitable solvents which will dissolve the binder resin, such as cyclohexane, methyl ethyl ketone, methyl isobutyl ketone, ethyl acetate, benzene, toluene, xylene, tetrahydrofuran, dioxane, and the like, can be used without any particular limitation. They may be used as a single solvent or a mixture of two or more Any other additives that are usually used in magnetic paint may also be used, for example, abrasive powders, anti-static agents, dispersants, colorants, and the like.

When the magnetic layer is formed only on one side of the non-magnetic support, a backing coat layer may be formed on the opposite side. The backing coat layer is formed by preparing a dispersion mixture as a paint which contains a non-magnetic powder such as carbon black or calcium carbonate and a binder resin such as vinyl chloride-vinyl acetate copolymer, polyurethane resin, cellulose resin or the like in an organic solvent. This paint is applied to the opposite side of the non-magnetic support and dried.

EXAMPLES

The present invention will be explained with the following examples. However, these are only representative of practical application examples of magnetic recording media, and the uses, manufacturing methods, or substances of the invention are obviously not limited thereto. Furthermore, the branched aliphatic diesters 1 to 8 used in each example were manufactured according to the Preparation Examples 1 to 8 below.

Fourier transform infra-red spectrometer (PI-1000 manufactured by Mattson) was used in the identification of the prepared branched aliphatic diesters.

Preparation Example 1

Versatic 10 (1.2 moles) and thionyl chloride (1.4 moles) were introduced into a round-bottomed flask and allowed to react in benzene as a solvent at 70° C. for 12 hours. After cooling, the reaction mixture was distilled under reduced pressure, and the acid chloride of Versatic 10 was obtained.

Then, a diethyl ether solution of the acid chloride obtained above (1.0 mole) was slowly dropwise added into a diethyl ether solution of 1H,1H,10H,10H-perfluoro-1,10-decanediol (0.4 mole) and pyridine (1.0 mole). On completion of the addition, a reaction was conducted at 40° C. for 24 hours. After cooling, the diethyl ether solvent was distilled off. After that, the product was washed with water and purified by a reduced pressure distillation to obtain the desired branched aliphatic diester 1.

The IR spectrum of the diester 1 is shown in FIG. 1, which confirms the production of the desired diester since the peak assigned to the ester linkage was found around 1740 $cm^{-1}$.

Preparation Example 2

Neodecanoic acid (1.2 moles) and thionyl chloride (1.4 moles) were introduced into a round-bottomed flask and allowed to react in benzene as a solvent at 70° C. for 12 hours. After cooling, the reaction mixture was distilled under reduced pressure, and an acid chloride of neodecanoic acid was obtained.

Then, a diethyl ether solution of the acid chloride obtained above (1.0 mole) was slowly dropwise added into a diethyl ether solution of 1H,1H,10H,10H-perfluoro-1,10-decanediol (0.4 mole) and pyridine (1.0 mole). On completion of the addition, a reaction was conducted at 40° C. for 24 hours. After cooling, the diethyl ether solvent was distilled off. After that, the product was washed with water and purified by a reduced pressure distillation to obtain the desired branched aliphatic diester 2. The production of the desired product was confirmed by the IR spectroscopy as in Example 1.

Preparation Example 3

Ekacid 13 (1.2 moles) and thionyl chloride (1.4 moles) were introduced into a round-bottomed flask and allowed to react in benzene as a solvent at 70° C. for 12 hours. After cooling, the reaction mixture was distilled under reduced pressure, and an acid chloride of Ekacid 13 was obtained.

Then, a diethyl ether solution of the acid chloride obtained above (1.0 mole) was slowly dropwise added into a diethyl ether solution of 1H,1H,10H,10H-perfluoro-1,10-decanediol (0.4 mole) and pyridine (1.0 mole). On completion of the addition, a reaction was conducted at 40° C. for 24 hours. After cooling, the diethyl ether solvent was distilled off. After that, the product was washed with water and purified by a reduced pressure distillation to obtain the desired branched aliphatic diester 3. The production of the desired product was confirmed by the IR spectroscopy as in Example 1.

Preparation Example 4

Versatic 10 (1.2 moles) and thionyl chloride (1.4 moles) were introduced into a round-bottomed flask and allowed to react in benzene as a solvent at 70° C. for 12 hours. After cooling, the reaction mixture was distilled under reduced pressure, and an acid chloride of Versatic 10 was obtained.

Then, a diethyl ether solution of the acid chloride obtained above (1.0 mole) was slowly dropwise added into a diethyl ether solution of 1H,1H,12H,12H-perfluoro-1,12-dodecanediol (0.4 mole) and pyridine (1.0 mole). On completion of the addition, a reaction was conducted at 40° C. for 24 hours. After cooling, the diethyl ether solvent was distilled off. After that, the product was washed with water and purified by a reduced pressure distillation to obtain the desired branched aliphatic diester 4. The production of the desired product was confirmed by the IR spectroscopy as in Example 1.

Preparation Example 5

Versatic 10 (1.2 moles) and thionyl chloride (1.4 moles) were introduced into a round-bottomed flask and allowed to react in benzene as a solvent at 70° C. for 12 hours. After cooling, the reaction mixture was distilled under reduced pressure, and an acid chloride of Versatic 10 was obtained.

Then, a diethyl ether solution of the acid chloride obtained above (1.0 mole) was slowly dropwise added into a diethyl ether solution of 1H,1H,2H,3H,3H-perfluorononane-1,2-diol (0.4 mole) and pyridine (1.0 mole). On completion of the addition, a reaction was conducted at 40° C. for 24 hours. After cooling, the diethyl ether solvent was distilled off. After that, the product was washed with water and purified by a reduced pressure distillation to obtain the desired branched aliphatic diester 5. The production of the desired product was confirmed by the IR spectroscopy as in Example 1.

Preparation Example 6

Versatic 10 (1.2 moles) and thionyl chloride (1.4 moles) were introduced into a round-bottomed flask and allowed to react in benzene as a solvent at 70° C. for 12 hours. After cooling, the reaction mixture was distilled under reduced pressure, and an acid chloride of Versatic 10 was obtained.

Then, a diethyl ether solution of the acid chloride obtained above (1.0 mole) was slowly dropwise added into a diethyl ether solution of 1H,1H,2H,3H,3H-perfluoroundecane-1,2-diol (0.4 mole) and pyridine (1.0 mole). On completion of the addition, a reaction was conducted at 40° C. for 24 hours. After cooling, the diethyl ether solvent was distilled off. After that, the product was washed with water and purified by a reduced pressure distillation to obtain the desired branched aliphatic diester 6. The production of the desired product was confirmed by the IR spectroscopy as in Example 1.

Preparation Example 7

Versatic 10 (1.2 moles) and thionyl chloride (1.4 moles) were introduced into a round-bottomed flask and allowed to react in benzene as a solvent at 70° C. for 12 hours. After cooling, the reaction mixture was distilled under reduced pressure, and an acid chloride of Versatic 10 was obtained.

Then, a diethyl ether solution of the acid chloride obtained above (1.0 mole) was slowly dropwise added into a diethyl ether solution of 1,10-decanediol (0.4 mole) and pyridine (1.0 mole). On completion of the addition, a reaction was conducted at 40° C. for 24 hours. After cooling, the diethyl ether solvent was distilled off. After that, the product was washed with water and purified by a reduced pressure distillation to obtain the desired branched aliphatic diester 7. The production of the desired product was confirmed by the IR spectroscopy as in Example 1.

Preparation Example 8

Tert-butylacetic acid (1.2 moles) and thionyl chloride (1.4 moles) were introduced into a round-bottomed flask and allowed to react in benzene as a solvent at 70° C. for 12 hours. After cooling, the reaction mixture was distilled under reduced pressure, and an acid chloride of tert-butylacetic acid was obtained.

Then, a diethyl ether solution of the acid chloride obtained above (1.0 mole) was slowly dropwise added into a diethyl ether solution of 1H,1H,10H,10H-perfluoro-1,10-decanediol (0.4 mole) and pyridine (1.0 mole). On completion of the addition, a reaction was conducted at 40° C. for 24 hours. After cooling, the diethyl ether solvent was distilled off. After that, the product was washed with water and purified by a reduced pressure distillation to obtain the desired branched aliphatic diester 8. The production of the desired product was confirmed by the IR spectroscopy.

Examples 1–16 and Comparative Examples 1–3

A 0.15 pm thick ferromagnetic metal thin film made from Co—O was formed by oblique vapor deposition of cobalt (Co) in an oxygen atmosphere on top of a 6 $\mu$m thick polyethylene terephthalate film. After that, a 20 $\mu$m thick DLC (diamond-like carbon) protective membrane was formed by the plasma polymerization method using an RF of 13.56 MHz along with ethylene as a monomer gas and hydrogen as a carrier gas. Finally, the product was cut to a width of 8 mm.

Next, each of the lubricants shown in Table 1 was dissolved in a mixed solvent of n-hexane, methyl ethyl ketone, and isopropyl alcohol in a volume ratio of 7:2:1 to give a concentration of 0.2 wt. %. (When an aliphatic amine was added, the aliphatic amine concentration was 0.05 wt. %.) The above-mentioned tape was immersed in and coated with the lubricant solution and then dried to give each of the videotapes having a lubricant coating on top of the DLC protective membrane.

The lubricants A, B and C used in Comparative Examples were as follows:

Lubricant A: 1,1-dihydroperfluorobutyl 2-isopropyl-2,3-dimethylbutanoate

Lubricant B: $H(CH_2)_6COOCH_2(CF_2)_8CH_2OCO(CH_2)_6H$

Lubricant C: $C_9H_{19}COOCH_2(CF_2)_2CH_2OCOC_9H_{19}$ ($C_9H_{19}$ being a mixture of branched isomer)

With each of the videotapes, still durability, a coefficient of friction and magnetic head-smudging were measured or evaluated as follows for the evaluation of lubricating properties:

<Still durability>

Each of the videotapes obtained in the Examples and Comparative Examples was preserved for 168 hours at 60° C. and 80% RH. Then, it was set at a winding angle of 220° around a 4 cm diameter cylinder for 8 mm videotapes at 20° C. and 50% RH.

Then, the playback output was measured in the still mode having recorded a sine wave with a wavelength of 1.6 $\mu$m with a tape tension of 12.5 gf/cm and a videotape/magnetic head relative speed of 11.3 m/s. The still life span was taken as the time when the playback output was reduced to half the initial value.

<Coefficient of friction>

Each of the videotapes obtained in the Examples and Comparative Examples was preserved for 168 hours at 60° C. and 80% RH. Then, the coefficient of friction was determined on the twentieth cycle of a reciprocal sliding test with a counter stainless steel pin at 20° C. and 50% RH and with a sliding speed of 1 m/min, a sliding distance of 5 cm and a tension of 20 g for 20 cycles.

<Magnetic head-smudging>

After each of the videotapes obtained in the Examples and Comparative Examples had been preserved at 60° C. and 80% RH for 168 hours, 50 cm of each videotape was evaluated after traversing repeatedly for 100 times at 20° C. and 50% RH in an 8 mm VCR (EV-S900, manufactured by Sony). The magnetic head-smudging was evaluated as follows:

A: no head-smudging

B: some head-smudging

C: substantial head-smudging.

The results are shown in Table 1.

TABLE 1

| Ex. No. | Lubricant Branched aliphatic diester | Aliphatic amine | Still durability (min.) | Coefficient of friction | Magnetic head-smudging |
|---|---|---|---|---|---|
| 1 | 1 | — | >180 | 0.24 | A |
| 2 | 2 | — | >180 | 0.23 | A |
| 3 | 3 | — | >180 | 0.26 | A |
| 4 | 4 | — | >200 | 0.28 | A |
| 5 | 5 | — | >200 | 0.23 | A |
| 6 | 6 | — | >200 | 0.26 | A |
| 7 | 7 | — | >160 | 0.28 | A |
| 8 | 8 | — | >120 | 0.30 | B |
| 9 | 1 | Stearylamine | >180 | 0.20 | A |
| 10 | 1 | N,N-Dimethyl-stearylamine | >180 | 0.22 | A |
| 11 | 5 | Stearylamine | >200 | 0.22 | A |
| 12 | 5 | N,N-Dimethyl-stearylamine | >220 | 0.24 | A |
| 13 | 7 | Stearylamine | >200 | 0.25 | A |
| 14 | 7 | N,N-Dimethyl-stearylamine | >200 | 0.27 | A |
| C. 1 | Lubricant A | | 20 | 0.25 | B |
| C. 2 | Lubricant B | | 120 | 0.30 | C |
| C. 3 | Lubricant C | | 40 | 0.27 | B |

Examples 15–28 and Comparative Examples 4–6

A 0.15 μm thick ferromagnetic metal thin film made from Co—Ni—O [Co:Ni (weight ratio)=80:20] was formed by the oblique vapor deposition of Co—Ni on a 10 μm thick ethylene terephthalate film under an oxygen atmosphere, and then cut to a width of 8 mm.

Then, each of the lubricants shown in Table 2 was dissolved in a mixed solvent of n-hexane, methyl ethyl ketone, and isopropyl alcohol in a volume ratio of 7:2:1 to give a concentration of 0.2 wt. %. (When an aliphatic amine was added, the concentration of the aliphatic amine was 0.05 wt. %.) The above-mentioned tape was immersed in the lubricant solution and the respective videotapes having a lubricant coating on the ferromagnetic metal thin film layer made.

With each of the videotapes, still durability, a coefficient of friction and magnetic head-smudging were measured in the same manners as described above. The results are shown in Table 2.

TABLE 2

| Ex. No. | Lubricant Branched aliphatic diester | Aliphatic amine | Still durability (min.) | Coefficient of friction | Magnetic head-smudging |
|---|---|---|---|---|---|
| 15 | 1 | — | >120 | 0.26 | A |
| 16 | 2 | — | >140 | 0.25 | A |
| 17 | 3 | — | >120 | 0.24 | A |
| 18 | 4 | — | >140 | 0.25 | A |
| 19 | 5 | — | >140 | 0.23 | A |
| 20 | 6 | — | >140 | 0.23 | A |
| 21 | 7 | — | >140 | 0.28 | A |
| 22 | 8 | — | >100 | 0.28 | B |
| 23 | 1 | Stearylamine | >140 | 0.21 | A |
| 24 | 1 | N,N-Dimethyl-stearylamine | >140 | 0.22 | A |
| 25 | 5 | Stearylamine | >140 | 0.22 | A |
| 26 | 5 | N,N-Dimethyl-stearylamine | >140 | 0.24 | A |
| 27 | 7 | Stearylamine | >120 | 0.25 | A |
| 28 | 7 | N,N-Dimethyl-stearylamine | >120 | 0.25 | A |
| C. 4 | Lubricant A | | 15 | 0.26 | B |
| C. 5 | Lubricant B | | 45 | 0.28 | C |
| C. 6 | Lubricant C | | 20 | 0.30 | B |

Examples 29–44 and Comparative Examples 7–9

A magnetic paint was prepared by mixing and dispersing α—Fe magnetic powder (coercive force, 1500 Oe; saturation magnetization, 120 emu/g) (100 wt. parts), a vinyl chloride-vinyl acetate-vinyl alcohol copolymer (VAGH of UCC) (20 wt. parts), a polyfunctional isocyanate compound (5 wt. parts), carbon black (3 wt. parts), α—$Al_2O_3$ powder (3 wt. parts), myristic acid (2 wt. parts), cyclohexanone (150 wt. parts) and toluene (130 wt. parts), in a ball mill for 72 hours.

Then, the magnetic paint was applied onto a 15 μm thick polyethylene terephthalate film so that it would have a thickness of 5 μm after drying. The film was then dried and a magnetic layer formed. After calendering, it was cut into 8-mm widths.

Then, each of the lubricants shown in Table 3 was dissolved in n-hexane, methyl ethyl ketone, and isopropyl alcohol in a volume ratio of 7:2:1 to give a concentration of 0.2 wt. %. (When an aliphatic amine was added, the concentration of the aliphatic amine was 0.05 wt. %.) The above-mentioned tape was immersed into the lubricant solution, dried, and thus each of the videotapes having a lubricant coat on the magnetic layer was made.

With each of the videotapes, still durability, a coefficient of friction and magnetic head-smudging were measured in the same manners as described above. The results are shown in Table 3.

TABLE 3

| Ex. No. | Lubricant Branched aliphatic diester | Aliphatic amine | Still durability (min.) | Coefficient of friction | Magnetic head-smudging |
|---|---|---|---|---|---|
| 29 | 1 | — | >220 | 0.23 | A |
| 30 | 2 | — | >220 | 0.24 | A |
| 31 | 3 | — | >220 | 0.25 | A |
| 32 | 4 | — | >240 | 0.26 | A |
| 33 | 5 | — | >240 | 0.23 | A |
| 34 | 6 | — | >240 | 0.23 | A |
| 35 | 7 | — | >220 | 0.27 | A |
| 36 | 8 | — | >180 | 0.28 | B |
| 37 | 1 | Stearylamine | >220 | 0.20 | A |
| 38 | 1 | N,N-Dimethyl-stearylamine | >240 | 0.23 | A |
| 39 | 5 | Stearylamine | >240 | 0.23 | A |
| 40 | 5 | N,N-Dimethyl-stearylamine | >240 | 0.23 | A |
| 41 | 7 | Stearylamine | >220 | 0.24 | A |
| 42 | 7 | N,N-Dimethyl-stearylamine | >240 | 0.25 | A |

TABLE 3-continued

| Ex. No. | Lubricant Branched aliphatic diester | Aliphatic amine | Still durability (min.) | Coefficient of friction | Magnetic head-smudging |
|---|---|---|---|---|---|
| | | stearylamine | | | |
| C. 7 | | Lubricant A | 30 | 0.25 | B |
| C. 8 | | Lubricant B | 100 | 0.29 | C |
| C. 9 | | Lubricant C | 20 | 0.32 | B |

As can be clearly seen from the results in Tables 1, 2 and 3, all the videotapes of Examples 1–42 had the still durability and coefficient of friction which were the same or better than those of the videotapes of comparative Examples 1–9 which used the conventional lubricants. Thus, the videotapes of the present invention have good cation properties.

Furthermore, the videotapes of Examples 1–42 caused magnetic head-smudging.

What is claimed is:

1. A lubricant comprising a branched aliphatic diester of the general formula:

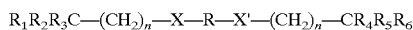

wherein $R_1$ to $R_6$ are the same or different and represent a hydrocarbon group having 1–8 carbon atoms;

R is a fluorinated hydrocarbon group having 6 to 18 carbon atoms;

either one of X and X' represent either one of —OCO— and —COO—, while the other of X and X' represent the other of —OCO— and —COO—; and n is an integer from 0 to 6.

2. The lubricant as claimed in claim 1, wherein said fluorinated hydrocarbon group for R is a straight fluorinated hydrocarbon group.

3. The lubricant as claimed in claim 1, wherein the branched aliphatic diester has a total of at least 20 carbon atoms.

4. A lubricant comprising a branched aliphatic diester of the general formula:

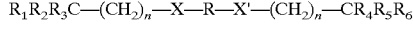

wherein $R_1$ to $R_6$ are the same or different and represent a hydrocarbon group having 1–8 carbon atoms;

R is a fluorinated hydrocarbon group having 6 to 18 carbon atoms; and n is an integer from 0 to 6, and an aliphatic amine of the general formula:

wherein $R_7$, $R_8$ and $R_9$ are the same or different and represent a hydrogen atom or a hydrogen group having 1 to 26 carbon atoms.

5. The lubricant according to claim 4 wherein R is selected from the group consisting of 1H,1H,10H,10H-perfluorodoc-(1,10)-yl, 1H,1H,12H,12H-perfluorododec-(1,12)-yl, 1H,1H,2H,3H,3H-perfluoronon-(1,2)-yl, and 1H,1H,2H,3H,3H-perfluoroundec-(1,2)-yl.

6. The lubricant according to claim 4 wherein $R_1R_2R_3C$—$(CH_2)_n$—CO and CO—$(CH_2)_n$—$CR_4R_5R_6$ are esterified forms of Versatic 10.

7. The lubricant as claimed in claim 4, wherein a molar ratio of the aliphatic amine to the branched aliphatic diester is between 100:1 and 0.01:1.

8. The lubricant as claimed in claim 4 or 7, wherein the total number of carbon atoms in the aliphatic amine is at least 12.

9. A magnetic recording medium comprising a non-magnetic support and a magnetic layer on at least one side of said non-magnetic support, wherein said medium contains a lubricant as claimed in claim 1 or 4 within or on the surface of the magnetic layer.

10. The magnetic recording medium as claimed in claim 9, wherein the magnetic layer is a ferromagnetic metal thin film layer, and 0.5–20 mg/m$^2$ of the lubricant is coated on the top of the ferromagnetic metal thin film layer.

11. The magnetic recording medium as claimed in claim 10, wherein a protective layer comprising at least one material selected from the group consisting of carbon, carbon nitride, silicon oxide, zirconium oxide, and chromium oxide is formed on the surface of the ferromagnetic metal thin film layer.

12. The magnetic recording layer as claimed in claim 9, wherein the magnetic layer is a coating type magnetic layer containing a magnetic powder, and 10–100 mg/m$^2$ of the lubricant is contained within the magnetic layer.

* * * * *